United States Patent [19]
Platt, Jr.

[11] Patent Number: 6,146,353
[45] Date of Patent: Nov. 14, 2000

[54] SMOKE EXTRACTION DEVICE

[75] Inventor: Robert C. Platt, Jr., Boulder, Colo.

[73] Assignee: Sherwood Services AG, Shaffhausen, Switzerland

[21] Appl. No.: 09/158,733

[22] Filed: Sep. 22, 1998

[51] Int. Cl.[7] .................................................. A61B 17/00
[52] U.S. Cl. .............................. 604/22; 604/35; 604/41; 604/313; 606/41; 606/170
[58] Field of Search .................................. 604/22, 35, 27, 604/289, 309, 310, 313; 606/41, 44, 45, 46, 47, 159, 167, 170, 171

[56] References Cited

U.S. PATENT DOCUMENTS

| | | |
|---|---|---|
| 3,825,004 | 7/1974 | Durden, III . |
| 3,828,780 | 8/1974 | Morrison, Jr. . |
| 3,902,494 | 9/1975 | Haberlen et al. . |
| 3,906,955 | 9/1975 | Roberts . |
| 3,974,833 | 8/1976 | Durden, III . |
| 4,562,838 | 1/1986 | Walker . |
| 4,640,279 | 2/1987 | Beard . |
| 4,642,128 | 2/1987 | Solorzano . |
| 4,683,884 | 8/1987 | Hatfield et al. . |
| 4,701,193 | 10/1987 | Robertson et al. . |
| 4,735,603 | 4/1988 | Goodson et al. . |
| 4,911,159 | 3/1990 | Johnson et al. . |
| 4,986,839 | 1/1991 | Wertz et al. . |
| 5,026,368 | 6/1991 | Adair . |
| 5,055,100 | 10/1991 | Olsen . |
| 5,071,418 | 12/1991 | Rosenbaum . |
| 5,147,292 | 9/1992 | Kullas et al. . |
| 5,160,334 | 11/1992 | Billings et al. . |
| 5,192,267 | 3/1993 | Shapira et al. . |
| 5,195,959 | 3/1993 | Smith . |
| 5,199,944 | 4/1993 | Cosmescu . |
| 5,224,944 | 7/1993 | Elliott . |
| 5,234,428 | 8/1993 | Kaufman . |
| 5,242,442 | 9/1993 | Hirschfeld . |
| 5,269,781 | 12/1993 | Hewell, III . |
| 5,318,516 | 6/1994 | Cosmescu . |
| 5,318,565 | 6/1994 | Kuriloff et al. . |
| 5,409,484 | 4/1995 | Erlich et al. . |
| 5,431,650 | 7/1995 | Cosmescu . |
| 5,451,222 | 9/1995 | De Maagd et al. . |
| 5,460,602 | 10/1995 | Shapira . |
| 5,868,768 | 2/1999 | Wicherski et al. ...................... 606/159 |
| 5,893,862 | 4/1999 | Prattt et al. ............................... 606/170 |
| 5,944,737 | 8/1999 | Tsonton et al. .......................... 606/205 |
| 5,951,581 | 9/1999 | Saadat et al. ............................ 606/170 |

FOREIGN PATENT DOCUMENTS

| | | |
|---|---|---|
| 2 235 669 | 1/1975 | France . |
| WO 94/20032 | 9/1994 | WIPO . |

*Primary Examiner*—Glenn K. Dawson
*Assistant Examiner*—David J. Cho

[57] ABSTRACT

A smoke extraction device for use with an electrosurgical instrument is provided. The smoke extraction device includes an elongated body portion defining a first lumen having first and second ends. The first end of the first lumen is adapted to be connected to a source of vacuum. A channel portion defining a second lumen is connected to the body portion. The channel portion defines a second lumen and includes an inlet opening which communicates with the first and second lumens. An attachment member is operatively secured to the elongated body portion. The attachment member is configured and dimensioned to releasably secure the smoke extraction device to a surgical instrument having a distally extending tool member. The attachment member is positioned on the elongated body such that when the smoke extractor device is releasably secured to a surgical instrument, the inlet opening of the channel portion is positioned below the tool member.

22 Claims, 4 Drawing Sheets

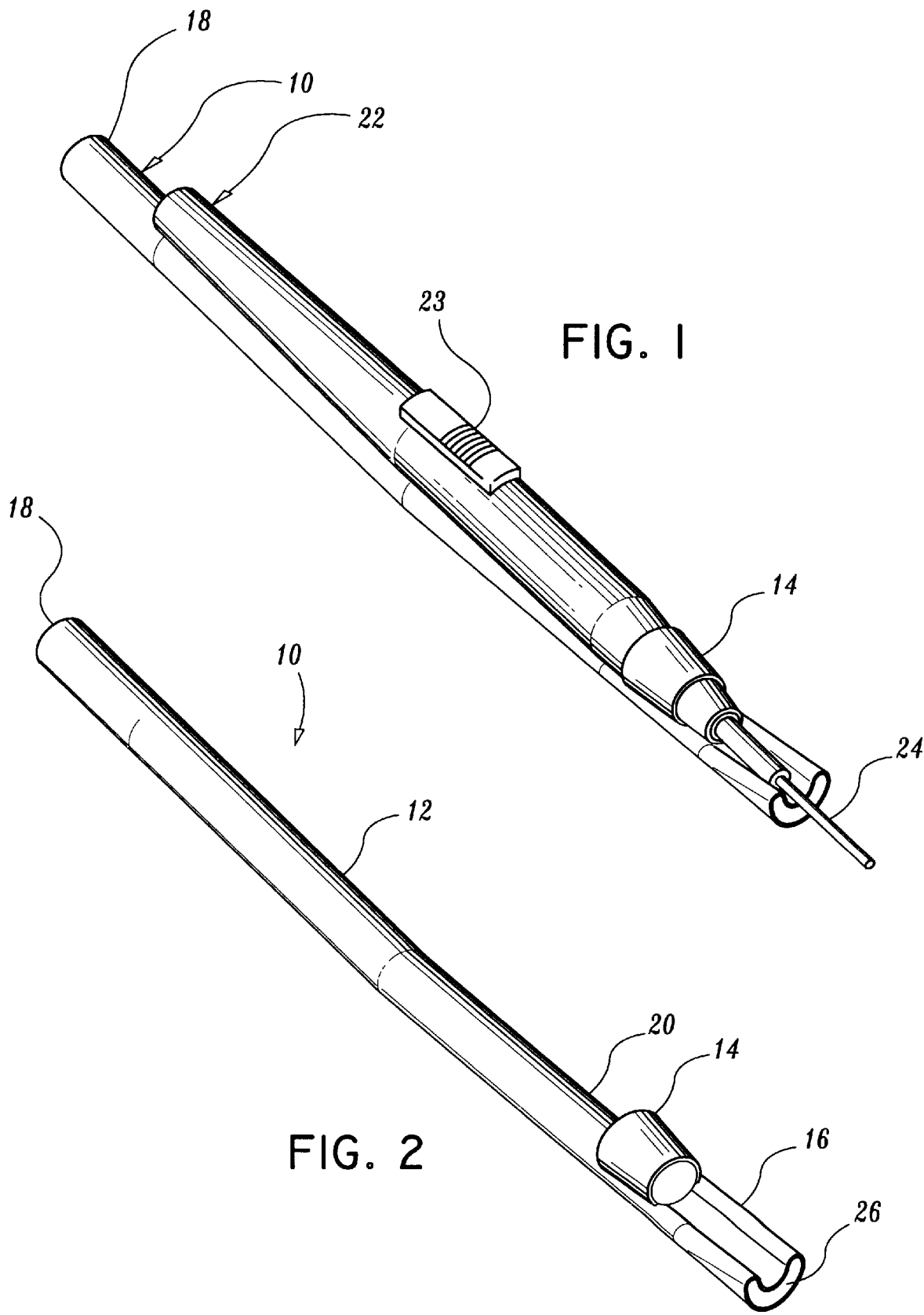

SMOKE EXTRACTION DEVICE

BACKGROUND

1. Technical Field

The present disclosure relates to a smoke extraction device for use during a surgical procedure. More specifically, the present disclosure relates to a smoke extraction device adapted to be attached to the handpiece of an electrosurgical instrument.

2. Background of Related Art

Modern surgical techniques require a variety of surgical instruments which generate smoke and/or fumes. These instruments include electrosurgical and laser surgical instruments for cutting and coagulating tissue. The generation of smoke and/or fumes at a surgical site creates a variety of problems. For example, smoke at the surgical site can impair the visibility of the surgeon increasing the difficulty of the surgery or necessitating the use of an assistant to clear the surgical site. The fumes may also cause noxious odors which may irritate those present at the surgery. Moreover, particulates released when tissue is burned can potentially carry bacteria and viruses.

Smoke extraction devices for use with electrosurgical and laser surgical instruments are well known. For example, U.S. Pat. No. 5,242,442 to Hirschfeld discloses a smoke aspirating electrosurgical device for incising and cauterizing anatomical structures. The device includes a handle and a blade attached to the forward end of the handle. An aspirating channel having a channel inlet positioned above the blade is formed in the handle. The channel is connected to a suction tube. During use, smoke produced by incision or cauterization is drawn into the channel inlet and evacuated through the suction tube.

U.S. Pat. No. 5,154,709 to Johnson discloses a vacuum hood attachment for electrosurgical instruments including an annular sleeve which is positioned about a cauterizing blade of an electrosurgical instrument. A vacuum outlet which communicates with the interior of the annular sleeve is adapted to be connected to a source of vacuum. When a surgical procedure is being performed, smoke is withdrawn from the surgical site through the annular sleeve of the vacuum hood attachment.

U.S. Pat. Nos. 5,085,657 and 5,451,223 to Ben-Simhon disclose electrosurgical instruments having a cutting/coagulating electrode and a suction tube adapted to be connected to a source of suction. The cutting/coagulating electrode is completely surrounded by and positioned within the frontal open end of the tube. During operation of the electrosurgical device, smoke generated at a surgical site is drawn over the cutting/coagulating electrode and removed through the suction tube.

One problem that exists with known smoke extraction devices is that when smoke is removed from the surgical site over the electrosurgical tool, e.g., incising or cauterizing blade, visibility at the surgical site may be obscured. Accordingly, a need exists for an improved smoke extraction device which can be inexpensively manufactured while still providing improved visibility and smoke collection at the surgical site.

SUMMARY

In accordance with the present disclosure, a smoke extraction device for use with an electrosurgical instrument is provided. The smoke extraction device includes an elongated body portion defining a first lumen having first and second ends. The first end of the first lumen is adapted to be connected to a source of vacuum. A channel portion defining a second lumen is connected to the body portion. The channel portion defines a second lumen and includes an inlet opening which communicates with the first and second lumens. An attachment member is operatively secured to the elongated body portion. The attachment member is configured and dimensioned to releasably secure the smoke extraction device to a surgical instrument having a distally extending tool member. The attachment member is positioned on the elongated body such that when the smoke extractor device is releasably secured to a surgical instrument, the inlet opening of the channel portion is positioned below the tool member. In a preferred embodiment, the inlet opening is substantially U-shaped. Alternately, the inlet opening can be a variety of shapes including rectangular, semi-circular, oval, etc.

BRIEF DESCRIPTION OF THE DRAWINGS

Various preferred embodiments are described herein with reference to the drawings, wherein:

FIG. 1 is a perspective view of one embodiment of the smoke extraction device positioned on an electrosurgical instrument;

FIG. 2 is a perspective view of the smoke extraction device shown in FIG. 1;

FIG. 9 is a perspective view of the smoke extraction device and surgical instrument shown in FIG. 7 in an assembled condition.

DETAILED DESCRIPTION OF PREFERRED EMBODIMENTS

Figure 3:
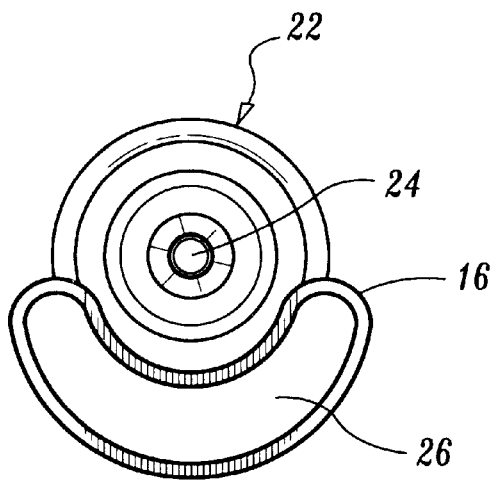
FIG. 3 is a front view of the channel inlet of the smoke extraction device shown in FIG. 1.

Preferred embodiments of the presently disclosed smoke extraction device will be described in detail with reference to the drawings, in which like reference numerals designate identical or corresponding elements in each of the several views.

FIGS. 1–3 illustrate one embodiment of the presently disclosed smoke extraction device shown generally as 10. Briefly, smoke extraction device 10 includes a tubular hollow body portion 12, an attachment member 14, and a substantially U-shaped channel portion 16. Tubular body portion 12 defines a lumen and has a first end 18 adapted to be connected to a source of vacuum (not shown) and a second end 20 in communication with U-shaped channel portion 16. Although not shown, first end 18 of tubular body portion 12 may include structure to facilitate attachment to the vacuum source, e.g., annular ribs, screw threads, etc.

Alternately, a suction hose can be clamped or frictionally secured directly to the exterior surface of first end 18 of tubular body portion 12.

Attachment member 14 is dimensioned and configured to receive an electrosurgical instrument 22. In a preferred embodiment, attachment member 14 includes a conical tube or ring dimensioned and configured to receive the tapered distal end of an electrosurgical instrument 22 having an actuator button 23. Alternately, other attachment members may be used in place of conical member 14. For example, a resilient band or an adjustable clamp (not shown) may be provided to attach the smoke extraction device to an electrosurgical instrument. Attachment member 14 should be spaced from the distal end of U-shaped channel portion 16 a sufficient distance so as not to obscure visibility of the tool 24, e.g., needle or blade electrode, cauterizing ball, etc., positioned at the distal end of electrosurgical instrument 22.

U-shaped channel portion 16 includes a substantially U-shaped inlet opening 26. Tubular body portion 12, attachment member 14 and U-shaped channel portion 16 are positioned in relation to each other to locate inlet opening 26 at a position proximal of and below tool 24 of electrosurgical instrument 22. Preferably, body portion 12, attachment member 14 and U-shaped channel portion 16 are monolithically formed from plastic, e.g., polystyrene, although multi-part construction using a variety of materials is also envisioned.

During use, smoke generated by incising and/or cauterizing tissue is evacuated from the surgical site adjacent tool 24 through U-shaped channel portion 16 and tubular body portion 12. Since inlet opening 26 is positioned below tool 24, visibility at the surgical site is not obscured by smoke evacuation device 10 or by smoke being drawn into inlet opening 26. Moreover, since inlet opening 26 is located near the site of smoke generation, improved smoke collection is achieved.

Figure 4:
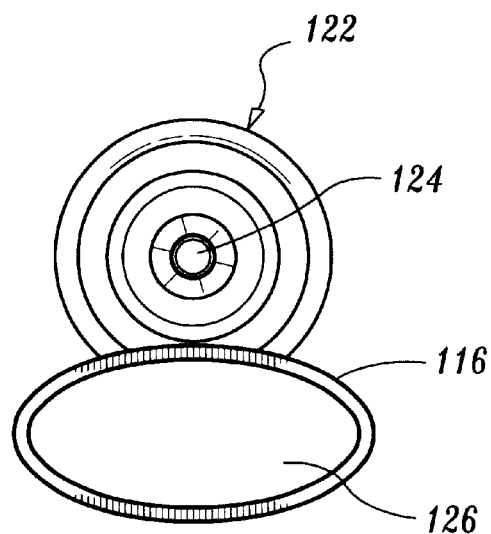
FIG. 4 is a front view of an alternate embodiment of the channel inlet of the presently disclosed smoke extraction device.
Figure 5:
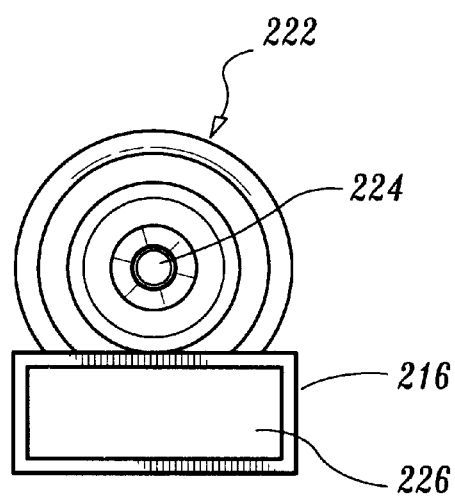
FIG. 5 is a front view of another alternate embodiment of the channel inlet of the presently disclosed smoke extraction device.
Figure 6:
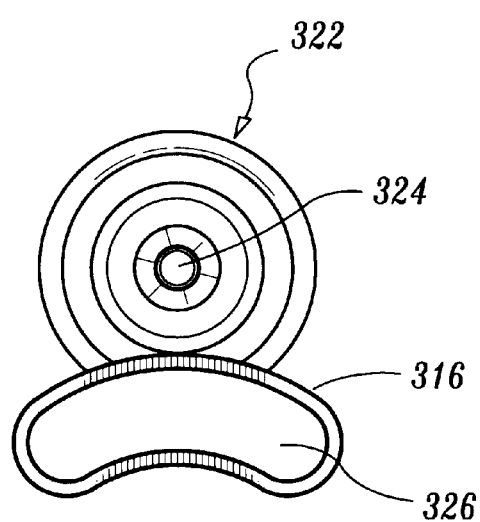
FIG. 6 is a front view of yet another alternate embodiment of the channel inlet of the presently disclosed smoke extraction device.

FIGS. 4–6 illustrate alternate embodiments of the presently disclosed smoke extraction device shown generally as 100, 200 and 300, respectively. Smoke extraction device 100 includes an oval inlet opening 126 that communicates with channel portion 116. Inlet opening 126 is positioned below tool 124 of electrosurgical device 122. Smoke extraction device 200 includes a rectangular inlet opening 226 which communicates with channel portion 216. Inlet opening 226 is positioned below tool 224 of electrosurgical device 222. Smoke extraction device 300 includes a semispherical inlet opening 326 that communicates with channel portion 316. Inlet opening 316 is positioned below tool 324 of electrosurgical device 322. Alternately, the channel portion may take on other configurations.

Figure 7:
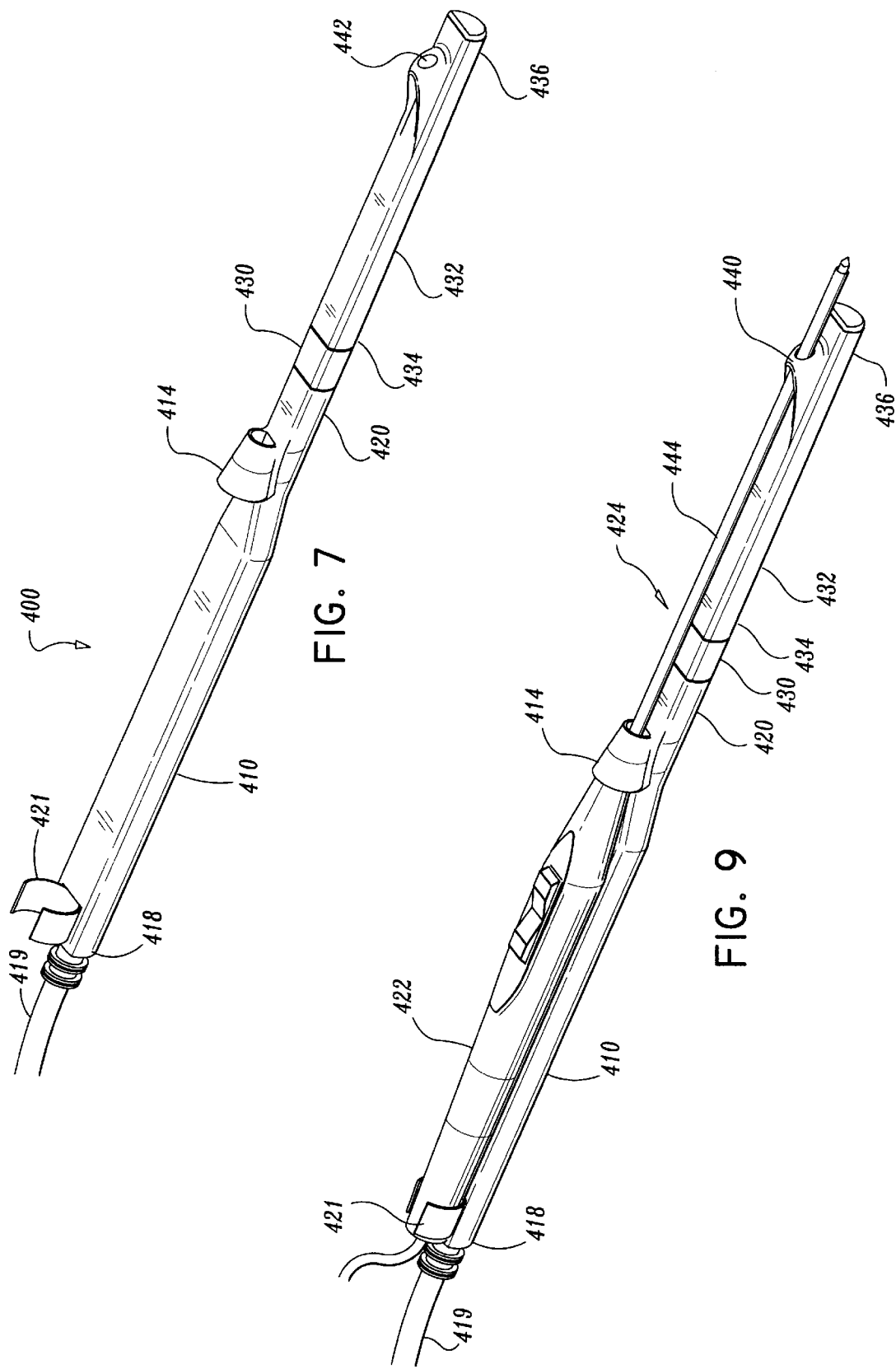
FIG. 7 is a perspective view of an alternate embodiment of the smoke extractor device.
Figure 8:
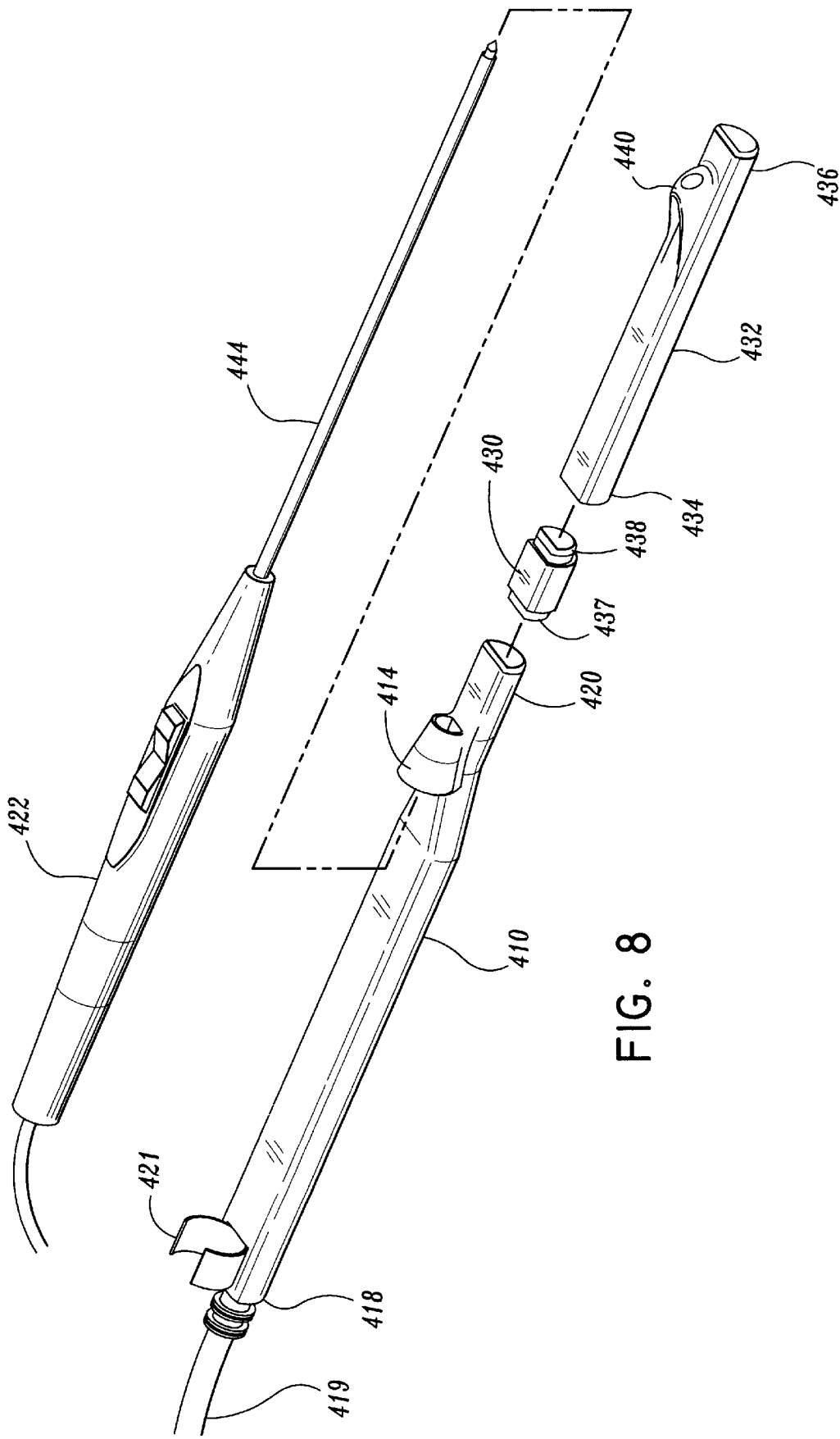
FIG. 8 is a perspective view with parts separated of the smoke extraction device shown in FIG. 7 with a surgical instrument.

FIGS. 7–9 illustrate an alternate embodiment of the presently disclosed smoke extraction device shown generally as 400. Smoke extraction device 400 includes an elongated hollow body portion 410, a hollow adapter 430, and an elongated hollow extension 432. Body portion 410 defines a lumen and has a proximal end 418 adapted to be connected to a source of vacuum (not shown) via a suction hose 419 and a distal end 420. An attachment member 414 configured to receive the distal end of an electrosurgical instrument 422 is secured to distal end 420 of body portion 410. A semi-cylindrical clamp 421 is secured to proximal end 418 of body portion 410. Clamp 421 is dimensioned and configured to receive the proximal end of an electrosurgical instrument to secure smoke extraction device 400 to instrument 422. Preferably, clamp 421 is constructed from a resilient material which frictionally engages surgical instrument 422 to securely fasten smoke extraction device 400 to instrument 422. Body portion 410, attachment member 414 and clamp 421 may be monolithically formed from a plastic material, e.g., polystyrene. Alternately, these elements may be formed separately and fastened together using any known fastening techniques, e.g., ultrasonic welding.

Hollow extension 432 defines a lumen and has a proximal end 434 and a distal end 436. Proximal end 434 is connected to distal end 420 of body portion 410 by adapter 430. Adapter 430 includes proximal and distal stepped portions 437 and 438, respectively (See FIG. 8). Proximal stepped portion 437 is dimensioned and configured to be frictionally secured within distal end 420 of body portion 410, and distal stepped portion 438 is dimensioned and configured to be frictionally received within proximal end 434 of extension 432.

A guide member 440 is positioned adjacent distal end 436 of extension 432. Guide member 440 includes a guide opening 442 configured to receive an extended portion 444 of tool 424 of electrosurgical instrument 422. Preferably, guide member 440 is monolithically formed with extension 432 from plastic, although the parts may be formed separately and from a variety of different materials.

Smoke extraction device 400 is suitable for use with a surgical instrument having an extended tool member. Body portion 410, adapter 430 and extension 432 can be easily secured together to accommodate extended portion 444 of instrument 422. Adapter 430 and extension 432 can also be easily removed from body portion 410 to accommodate a surgical instrument, e.g., instrument 22 of FIG. 1, not having an extended tool member. Alternately, body portion 410, adapter 430 and extension 432 can be monolithically formed and suitable only for use with a surgical instrument having an extended tool member.

Distal end 436 of extension 432 defines an opening 426 which is positioned below tool member 424 when smoke extraction device 400 and surgical instrument 422 are fastened together. During use, smoke generated by incising and/or cauterizing tissue is evacuated from the surgical site adjacent tool 424 through extension 432, adapter 430 and body portion 410. As discussed above with respect to extraction device 10, since opening 426 is positioned below tool 424, visibility at the surgical site is not obscured by smoke evacuation device 400 or by smoke being drawn into inlet opening 426.

It will be understood that various modifications may be made to the embodiments herein. For example, the smoke extraction device may be adapted for use with a laser surgical instrument. Also, the body portion and the attachment member may take on any configuration capable of performing the above-described functions. Therefore, the above description should not be construed as limiting, but merely as exemplifications of preferred embodiments. Those skilled in the art will envision other modifications within the scope and spirit of the claims appended hereto.

What is claimed:

1. A smoke extraction device comprising:
    an elongated body portion defining a first lumen having a longitudinal axis and having first and second ends, the first end being adapted to be connected to a source of vacuum;
    a channel portion connected to the second end of the elongated body portion, the channel portion having an inlet opening which communicates with the first lumen;
    an attachment member operatively secured to the elongated body portion, the attachment member being configured and dimensioned to releasably secure the smoke extractor device to a surgical instrument having a distally extending tool member, wherein the attachment member is operatively positioned on the elongated body such that when the smoke extractor device is releasably secured to a surgical instrument, the inlet opening of the channel portion is positioned substantially below the tool member at a location to inhibit the flow of smoke over the tool member during a surgical procedure;

elongated extension defining a second lumen having a longitudinal axis aligned with the longitudinal axis of the first lumen; and an adapter having a first end configured to engage the elongated body portion and a second end configured to engage the elongated extension.

2. The smoke extraction device according to claim 1, wherein the elongated body portion, the channel portion and the attachment member are of monolithic construction.

3. The smoke extraction device according to claim 2, wherein the smoke extraction device is constructed of plastic.

4. The smoke extraction device according to claim 1, wherein the attachment member is a conical member having a conical bore configured to receive an electrosurgical instrument.

5. The smoke extraction device according to claim 1, wherein the inlet opening is substantially U-shaped.

6. The smoke extraction device according to claim 1, wherein the inlet opening is substantially rectangular.

7. The smoke extraction device according to claim 1, wherein the inlet opening is substantially oval.

8. The smoke extraction device according to claim 1, wherein the elongated body portion is substantially tubular.

9. The smoke extraction device according to claim 1, wherein a guide member having a guide opening is formed at the distal end of the elongated extension, the guide opening being dimensioned to allow passage of the tool member.

10. The smoke extraction device according to claim 1, wherein the longitudinal axis of the first lumen is coaxial with the longitudinal axis of the second lumen.

11. A smoke extraction device comprising:

a body portion defining a first lumen, the body portion being adapted to be connected to a source of vacuum;

a channel portion connected to the body portion and defining a second lumen in communication with the first lumen, the second lumen having a substantially U-shaped inlet opening; and an attachment member including a conical member secured adjacent to the channel portion and a resilient clamp secured to the body portion the attachment member being configured and dimensioned to releasably secure the smoke extractor device to a surgical instrument having a distally extending tool member.

12. The smoke extraction device according to claim 11, wherein the attachment member is is positioned to locate the inlet opening of the channel portion below the tool member.

13. The smoke extraction device according to claim 11, wherein the body portion, the channel portion and the attachment member are of monolithic construction.

14. A smoke extraction device comprising:

an elongated body portion defining a first lumen and having first and second ends, the first end being adapted to be connected to a source of vacuum;

a channel portion connected to the second end of the elongated body portion, the channel portion having an inlet opening which communicates with the first lumen;

an attachment member operatively secured to the elongated body portion, the attachment member being configured and dimensioned to releasably secure the smoke extractor device to a surgical instrument having a distally extending tool member, wherein the attachment member is positioned such that the inlet opening does not extend above the tool member, the channel portion being located so as to provide unobscured visibility at the surgical site;

an elongated extension defining a second lumen; and an adapter having a first end configured to releasably engage the elongated body portion and a second end configured to releasably engage the elongated extension, wherein the first lumen and the second lumen are coaxial.

15. The smoke extraction device according to claim 14, wherein the elongated body portion, the channel portion and the attachment member are of monolithic construction.

16. The smoke extraction device according to claim 15, wherein the smoke extractor device is constructed of plastic.

17. The smoke extraction device according to claim 14, wherein the attachment member is a conical member having a conical bore configured to receive an electrosurgical instrument.

18. The smoke extraction device according to claim 14, wherein the inlet opening is substantially U-shaped.

19. The smoke extraction device according to claim 14, wherein the inlet opening is substantially rectangular.

20. The smoke extraction device according to claim 14, wherein the inlet opening is substantially oval.

21. The smoke extraction device according to claim 14, wherein the elongated body portion is substantially tubular.

22. The smoke extraction device according to claim 14, wherein a guide member having a guide opening is formed at the distal end of the elongated extension, the guide opening being dimensioned to receive the tool member.

* * * * *